United States Patent [19]

Queener

[11] 4,141,546
[45] Feb. 27, 1979

[54] MINI-COLLATOR/SORTER

[75] Inventor: Carl A. Queener, Boulder County, Colo.

[73] Assignee: International Business Machines Corporation, Armonk, N.Y.

[21] Appl. No.: 785,719

[22] Filed: Apr. 7, 1977

Related U.S. Application Data

[63] Continuation-in-part of Ser. No. 710,835, Aug. 2, 1976, abandoned.

[51] Int. Cl.² ..................... B65H 29/60; B65H 31/24
[52] U.S. Cl. .................................... 271/173; 271/80; 271/207
[58] Field of Search ................. 271/173, 181, 212, 80, 271/64, 177, 207; 209/74 R; 270/58

[56] References Cited

U.S. PATENT DOCUMENTS

| | | | |
|---|---|---|---|
| 1,237,646 | 8/1917 | Hollerith | 209/110 |
| 2,076,391 | 4/1937 | Whitehead | 271/64 |
| 2,241,168 | 5/1941 | Truitt et al. | 271/64 |
| 2,328,317 | 8/1943 | Wentworth | 271/64 X |
| 2,661,209 | 12/1953 | McGalliard | 271/173 |
| 2,856,182 | 10/1958 | Cantrell | 270/57 |
| 2,906,196 | 9/1959 | Ritzerfeld et al. | 271/64 X |
| 2,919,917 | 1/1960 | Worswick | 271/173 |
| 3,283,705 | 11/1966 | Niesen et al. | 271/64 X |
| 3,315,957 | 4/1967 | Mazzio et al. | 271/64 |
| 3,356,362 | 12/1967 | Mestre | 271/64 X |
| 3,414,254 | 12/1968 | Snellman et al. | 271/173 |
| 3,497,207 | 2/1970 | Caldwell et al. | 271/173 |
| 3,604,321 | 9/1971 | Snellman et al. | 271/173 X |
| 3,685,819 | 8/1972 | Deutsch | 271/173 |
| 3,704,793 | 12/1972 | Nicol et al. | 271/207 X |
| 3,788,640 | 1/1974 | Stemmle | 271/64 |
| 3,845,949 | 11/1974 | Acquaviva et al. | 271/64 |
| 3,847,391 | 11/1974 | Brant et al. | 271/220 |
| 3,918,701 | 11/1975 | Lee | 271/181 |
| 3,998,450 | 12/1976 | Howard | 271/173 |

Primary Examiner—Bruce H. Stoner, Jr.
Attorney, Agent, or Firm—Carl O. Barth

[57] ABSTRACT

The invention relates to a small collator/sorter adaptable for use with a document producing machine such as a copier and having particular utility as the only output receptacle. The collator/sorter is a multi-pocket device with a limited number of bins, each of which has a limited copy capacity and is well suited to be constructed and arranged as an integral part of a copier serving as a replacement for the conventional exit tray. The paper bins are preferably contained within a small space such that they can be unloaded in a one hand operation.

22 Claims, 14 Drawing Figures

MINI-COLLATOR/SORTER

CROSS-REFERENCE TO RELATED APPLICATION

This is a continuation-in-part application of Ser. No. 710,835, filed Aug. 2, 1976, and now abandoned, by Carl A. Queener, assigned to the same assignee as the present invention.

BACKGROUND OF THE INVENTION

1. Field of the Invention

The invention relates to the field of document collators and sorters particularly useful for office or convenience copiers and is especially well suited for use as the output copy receptacle of document producing machines. The primary utility presently contemplated for the collator/sorter of this invention is in combination with a convenience copier thus providing a compact copier-collator apparatus able to fulfill a very high percentage of customer requirements. However, the present invention is not necessarily limited to this application. Further, the present invention relates to a collator/sorter adapted to be operated and unloaded with one hand.

2. Prior Art

The term "collator" as used throughout the following specification shall mean a collator/sorter able to perform a variety of sheet distribution functions or modes which include but are not limited to a collate mode in which successive sheets are fed into separate, preferably adjacent sheet receiving bins and a sort or exit pocket mode in which each of the sheet receiving bins is filled to a determinable number of sheets.

Office copiers conventionally provide an output tray into which copies are stacked in uncollated order. If a collate function is required, a separate collate device is normally placed adjoining the copier and the copier's output feed would then selectively exit to either the copier's output tray or the collator. Those collators are frequently of the type providing up to a hundred individual bins, each bin having a sheet holding capacity of as much as one hundred sheets.

Various sheet delivery structures have been employed in the prior art collators. For instance, some prior art collators employ a pivotable ramp having a large number of paper receptacle bins sometimes arranged in multiple stacks. Such a collating device is a comparably extensive and expensive machine itself, being larger than a convenience copier and, therefore, not at all suitable to be an integral part of an office copier. Examples of such pivoted distributors are shown in U.S. Pat. Nos. 2,076,391 by Whitehead and 2,856,182 by Cantrell.

Other prior art devices employ a conveyor belt system to transport the sheets along the entrances of the paper bins with a deflector finger provided at each entrance which, when activated, deflects the sheet into the appropriate bin. The provision of various deflectors and the number of sheet receiving bins make such a collator unable to meet the requirements for a small and inexpensive output system for a convenience copier. Furthermore, it is neither possible to unload this kind of sorter from top nor to remove a stack of sheets with one hand. Additionally, the complexity of various motors and actuating devices require an equally complex controlling system which makes a sorter of this type even less suitable to be used as the only output system of an office copier. Examples of such multiple deflector collators are shown in U.S. Pat. Nos. 1,237,646 by Hollerith and 2,661,209 by Mc Galliard. Such sorter devices can be implemented with horizontal or vertical receiving bins as shown in U.S. Pat. No. 2,906,196 by Ritzerfeld et al.

Still other prior art collators employ a moving bin collator receiving sheets from a copying machine by moving past a copy discharge zone. While this design does not need any copy conveyor to feed the copies into the respective bins, the relatively complicated drive system for the moving bins as well as its size makes it unsuitable to be used as an integrated output system of a convenience copier. Additionally the copies cannot be conveniently unloaded and the bulky structure which must be physically moved render such devices slow in operation. An example of such a device is U.S. Pat. No. 2,241,168 by Truitt et al.

Finally, single moving deflector collators have been developed which have reasonable operating speed and reliability for many applications. A primary example of this approach is taught by prior art Wentworth U.S. Pat. No. 2,328,217 which describes a large collator adapted for collating sheets or distributing similar objects into a multiple shelved receiver. These receptacle shelves or bins are arranged in spaced parallel relation to each other forming a column or stack. All bin openings or mouths are ordered in a straight course or path, along which the articles to be distributed are transported by a conveyor system composed of continuous or closed loop belts. The articles to be collated are positively retained betweeen these continuous belts for transport along the straight course. This conveyor system is continuously driven by a first motor mounted to the frame of the collator. To divert or deflect the articles to be distributed into the respective bins, a single deflector assembly is operatively associated with the conveyor and is mounted for movement along the conveyor in the same path as the articles along the entrance mouths of the bins. Movement of this deflector assembly is accomplished by a cable system driven over a reversing clutch by a second motor mounted to the collator frame. An indexing mechanism controls positioning of the deflector assembly at predetermined positions along the conveyor path or course for deflecting moving articles therefrom into selected ones of the receiver shelves. Since the articles to be collated are positively held by the belt-like conveyor system up to the openings of the slightly sloped shelves, the Wentworth collator is substantially independent of particular horizontal or vertical orientations of the device.

The prior art discussed shows the existence of a large number of solutions for collators of different sizes and designs. However, it is clearly recognizable that none of these collators is suited to be integrated into an office copier.

The general object of this invention is to achieve a reliable and small collator/sorter design adaptable for many applications but especially suitable for use within a convenience copier.

Another object of this invention is to combine a convenience copier with a small and compact collator/sorter, thus providing a collating convenience copier.

A further object is to provide a collating copier unloadable from the top for easy access and better control.

An additional object is to provide a copier with an output copy collator which can be conveniently unloaded in a one hand operation in either the collate or non-collate mode.

Another object of the invention is to satisfy most of a user's collation needs with a device of lower cost than the prior art collators.

A further object is to eliminate the need for a separate exit pocket of a convenience copier equipped with a collator.

An additional object is to provide a copier with an output copy collator delivering staggered sets of collated copies.

SUMMARY OF THE INVENTION

The invention achieves these and other objects by a mini-collator particularly useful to function as the only output copy tray of a convenience copier and being constructed and arranged in a manner well suited for use as an integral part of the copier. The collator includes a relatively small number of sheet receiving bins, each of which has a limited capacity. The collator can be used in two modes, a collate mode, wherein successive sheets are fed into adjacent bins or a non-collate or sort mode wherein each of the bins is filled to a predetermined number of sheets. The sheet receiving bins are essentially vertically arranged and have a bottom opening which allows sheet insertion and a second, preferably top opening for manual sheet removal. A sheet transport system extends along the bottom openings of the bins and a travelling sheet deflector, movable along this transport system, deflects the sheets selectively into the bins. A manually selectable control means carries out the two above mentioned modes, the collate and the sort mode.

The foregoing and other features of the invention as well as its advantages and applications will be apparent from the following detailed description of the preferred embodiment which is illustrated in the accompanying drawings.

BRIEF DESCRIPTION OF THE DRAWINGS

FIGS. 1A and 1B compare a prior art arrangement with the present invention.

DESCRIPTION OF THE PREFERRED EMBODIMENT

Figure 1A:
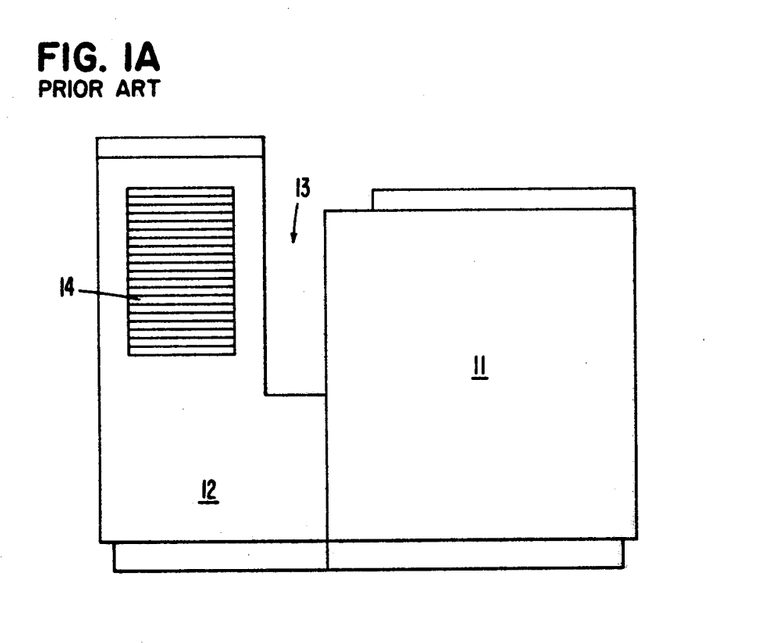
Figure 1B:
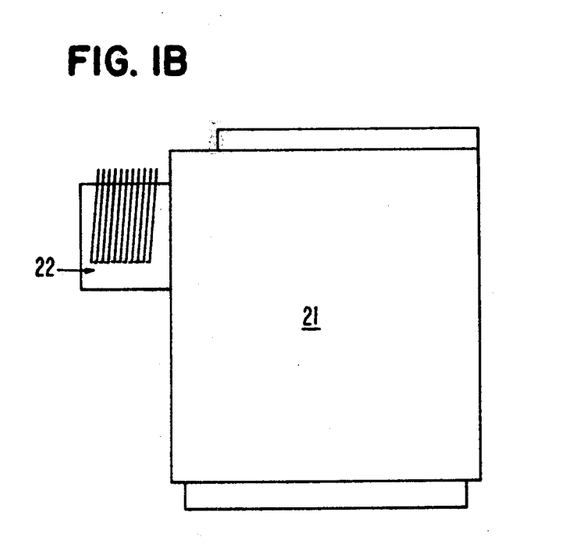

FIG. 1A shows an arrangement of a commercially available copier 11 with a typical prior art collator 12 attached. This example collator 12 may have twenty bins 14, each with a capacity of fifty sheets. FIG. 1B, on the other hand, is a schematic representation of the same commercial copier 21, implementing an exemplary version of the described preferred embodiment of the invention, the mini-collator 22 having ten bins each with a capacity of twenty sheets. Comparing FIGS. 1A and 1B, the advantages in compactness of the invention are obvious. The following table shows some approximate comparative figures:

|  | Weight kp (lbs.) | Height m (in.) | Width m (in.) | Depth m (in.) |
| --- | --- | --- | --- | --- |
| Example Collator of FIG. 1A | 136 (300) | 1.3 (51) | 0.84 (33) | 0.58 (23) |
| Mini-collator of FIG. 1B | 18 (39) | 0.3 (12) | 0.22 (9) | 0.51 (20) |

Those skilled in the art will recognize that the much smaller size and weight of the mini-collator 22 as shown in FIG. 1B and the operating structure described in detail below means that collator 22 generally can be manufactured at lower cost than the conventional prior art collator 12 of FIG. 1A.

It would appear from a superficial comparison that the integrated mini-collator 22 as shown in FIG. 1B is disadvantaged relative to the prior art collator 12 of FIG. 1A concerning the number of bins as well as the bin capacity. That is, the preferred embodiment of the invention has only ten bins instead of twenty of the example, and each bin has a capacity of only twenty sheets instead of fifty. However, it is important to assess the magnitude of these disadvantages relative to the user and his collation needs. It can be shown for typical office environment convenience copiers that the integrated mini-collator 22 of FIG. 1B satisfies the collation requirements of approximately 97% of the "walk-up" jobs, whereas the larger capacity prior art collator 12 satisfies the collation requirements for approximately 99% of the "walk-up" jobs. Thus, the capacity disadvantage of the small integrated mini-collator 22 results in a loss of only approximately 2% of jobs that can be executed. That means the shown implementation of the invention achieves its advantages of compactness and cost with only a minimal decrease in performacne.

Another attachable collator which is commercially available stacks the copies face up, i.e. with the tonered and fused side of the copy sheet visible in the collator bin. To achieve a correct order of the collated copies, this mode of collation requires the originals to be fed in reverse order, starting with the original's last page and finishing with its first page. Thus, the copies in the collator will be stacked correctly, but, when using a copier with an automatic or semi-automatic document feed, the originals will be in reverse order after copying. In most cases, this reversed document set needs to be rearranged, which can be done either manually or with an automatic document turnover mechanism or flipper. Obviously, both methods of rearrangement require either time or additional financial investment.

FIG. 1B, on the other hand, shows an incorporation of the present invention. The mini-collator 22 is integrated into the copier 21, which may be the same as shown in FIG. 1A. The mini-collator 22, being the only output receptacle of the copier 21, is either used as a normal exit pocket in a sort mode or as a collator in a collate mode. In either mode, it allows easy access for the operator. As the copies are stacked face down, i.e. facing to the right, in the collator bins, the collated sets of copies will have the same order as the set of originals fed manually or by an automatic or semi-automatic document feed. Thus, a document flipper is not necessary. Obviously, the mini-collator 22 requires much less space than the collator 12 shown in FIG. 1A. Material as well as financial investment are considerably lower. Nevertheless, this mini-collator 22 is able to execute most of the jobs that require a collator, and, perhaps, an additional document flipper.

Figures 1C, 2:
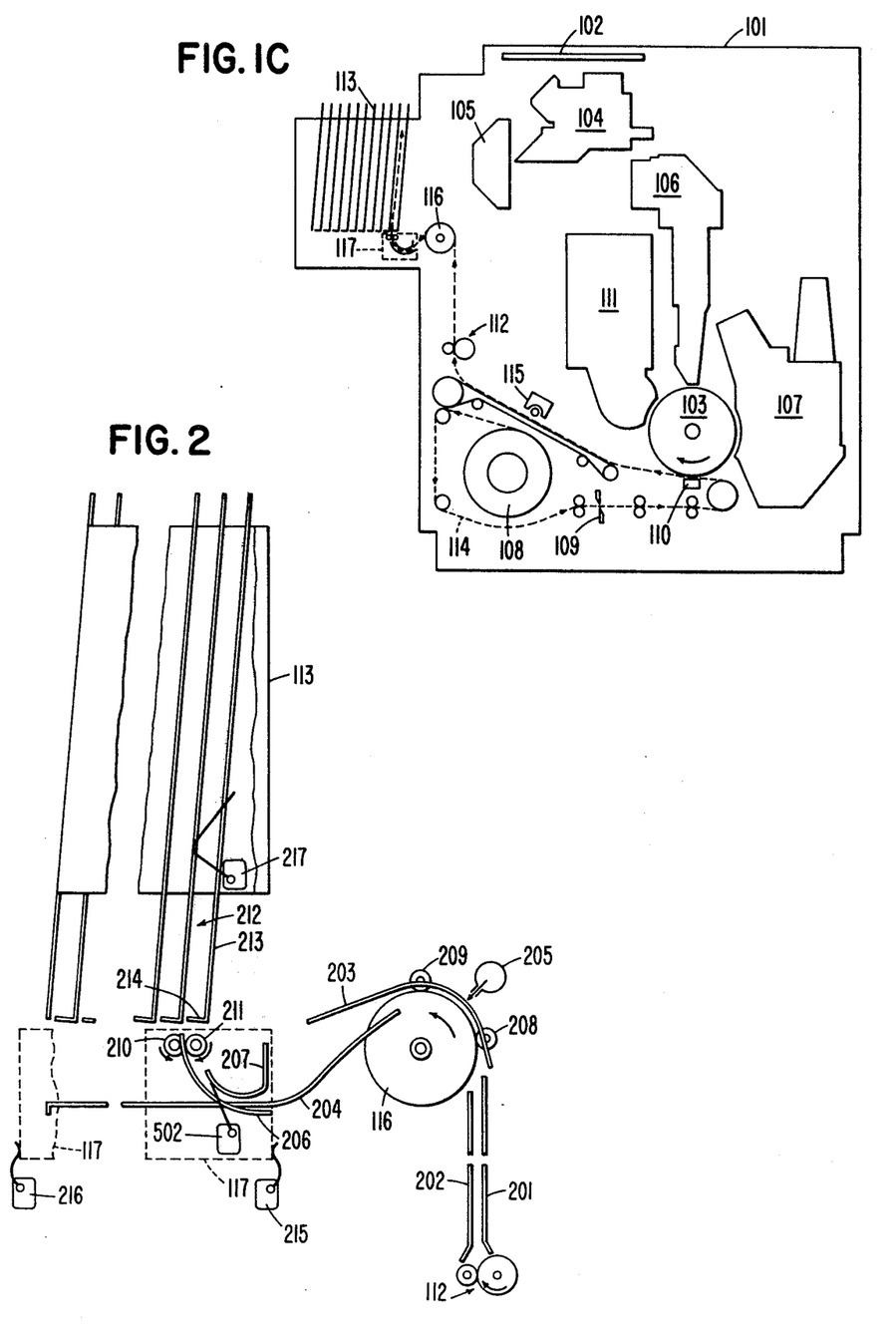
FIG. 1C is a schematic view of a xerographic copier incorporating the present invention.
FIG. 2 shows the copy paper path into the collator.

FIG. 1C shows a schematic view of a xerographic copier 101 comprising the present invention. A document which is to be copied is placed on the document glass 102 and imaged via the optical system 104, 105, and 106 onto the xerographic drum 103 which has been precharged by a (not shown) precharge unit. The exposition of xerographic drum 103 decharges it partly, so that a latent electrostatic image is formed on the photoconducting drum 103. The image is developed by developing station 107. In the meantime, paper has been fed through paper path 114 from paper roll 108 to cutting knife 109 where it is cut to sheets of the desired length. In a transfer station with the transfer corona 110, the developed or tonered image is transferred to the sheet of paper. After that, the remaining toner is cleaned off the photoconductor drum 103 by cleaning station 111. Additionally, the entire surface of the drum is exposed to light to dissipate the electrostatic charge. The photoconductor is now ready for the following cycle.

In the meantime, the toner transferred to the paper is fused, i.e. heated and melted onto the paper, in fusing station 115. The thus produced copy is now fed via the transport roll pair 112 over roll 116 to the movable deflector 117 into one of the bins of collator 113.

The above is a very general description of a copier which can be modified in various aspects. For example, the roll paper supply can be replaced by a cut sheet paper supply; the schematically depicted radiant fuser can be substituted by a hot roll fuser and the transport system does not necessarily need to be a vacuum system. These and other changes as well as additional stations, e.g. a paper detach arrangement to loosen the paper from the xerographic drum 103 or a copy discharge station, are well known and can be used by anybody skilled in the art as necessary.

FIG. 2 shows the paper path of the copy after fusing and the collator in more detail. A copy is fed through the nip of the transport roll pair 112 and enters the space between the two vertical paper baffles 201 and 202, serving as a vertical guide for the copy which is then fed over roll 116, supported by small rolls 208 and 209, with guide 203 being included to direct the copy movement in the event it prematurely detaches from roll 116. The distance between the transport roll pair 112 and nip between rolls 208 and 116 is chosen shorter than the appropriate length of a copy to be fed. To lower the temperature of the copies, cooling air is forced by a blower (not shown) into cooling plenum 205 and exits therefrom through a slot or perforations in the deflector guide 203 onto the copies as well as onto roll 116.

Roll 116 may be used to accelerate the copy speed. Whereas, for example, the copy speed in the paper path before roll 116 may be approximately 24 centimeters per second (9.3 inches per second), it may be accelerated to 76 centimeters per second (30 inches per second). This acceleration may be necessary for proper stacking of the copies in collator 113. This is due to the fact that the movable deflector 117 needs some time to step from bin to bin and back from the last bin into its initial position.

The copy, accelerated by roll 116, is now stripped from roll 116 and channelled outwardly by main guide 204, any prematurely stripped documents being redirected by the deflector guide 203 towards main guide 204.

All guides mentioned till now, the two vertical baffles 201 and 202, the deflector guide 203, and the main guide 204 are basically stationary with regard to the copier/collator frame, though they may be pivotable or otherwise removable for the clearance of paper jams.

When the copy which is moving on main guide 204 reaches the movable deflector unit 117, it is intercepted by the lower deflector guide 206 which partially extends through slits in main guide 204 into the nip between the two deflector drive rolls 210 and 211. The copy is held down by upper deflector guide 207. Both guides 206 and 207 as well as the drive rolls 210 and 211 are movable together with the deflector unit 117. Thus, these parts remove and feed each copy they receive from stationary main guide 204 into the bin 212 which is above them.

Figure 8:
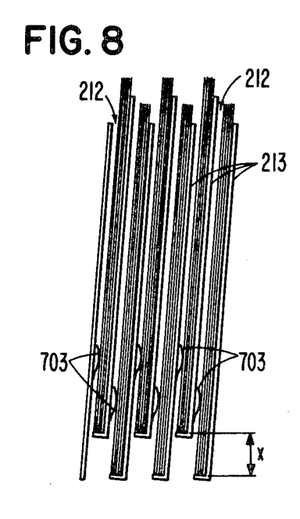
FIG. 8 shows an arrangement to achieve staggered sets of collated copies.

Each bin 212 consists essentially of two slightly inclined walls 213, one of which has on its lower end a lip 214 extending toward the other wall, leaving a small slit or mouth open to allow paper feeding into the bin. The copy is fed into the bin 212 with a speed high enough to move its trailing edge a little way into the bin. As bin 212 is slightly inclined, the inserted copy falls towards wall 213, its trailing edge resting on lip 214. FIG. 8 shows some bins 212 with inserted sheets. The bin walls 213 are shorter than the sheets, allowing easy manual removal of the inserted sheets after execution of the job. As will be shown later, each bin 212 may include retainer means that improve the resting of the copies against the wall with the lip. Since roller 116 accelerates the copies, the gap between two successive copies is increased to allow the collator's movable deflector unit 117 to step from bin to bin and to be transported back from the last bin (the left bin in FIG. 2) to its shown position under the first bin.

Figure 5:
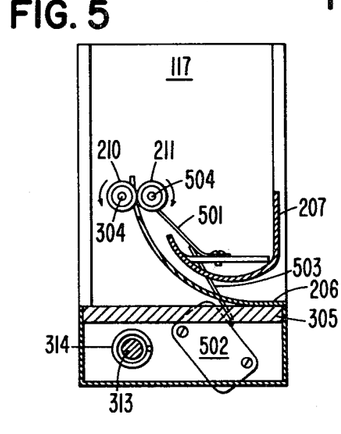
FIG. 5 is a cross-section of the deflector unit along line 5—5 in FIG. 3.

Furthermore, FIG. 2 shows a number of switches used to provide input signals for the logic described below in connection with FIGS. 9 and 10. Deflector-home switch 215 is arranged to provide an output signal when deflector unit 117 is in its home position under the first, i.e. right-most bin in FIG. 2. Similarly, last-bin-position switch 216 provides an output signal as soon as the deflector unit 117 reaches the left-most position (FIG. 2), having arrived under the last bin of the collator. Copy-in-bin switch 217 is associated with the first bin 212 of the collator and provides an output signal when the first bin 212 contains a copy. To facilitate handling, the feeler of copy-in-bin switch 217 allows reinsertion of a copy into the bin. Deflector switch 502 which is shown in more detail in FIG. 5, provides a signal when a copy is transported through deflector unit 117. The output signals of all switches mentioned before are inputted into the logic circuits shown in FIGS. 9 and 10 and discussed in connection therewith.

Figure 3:
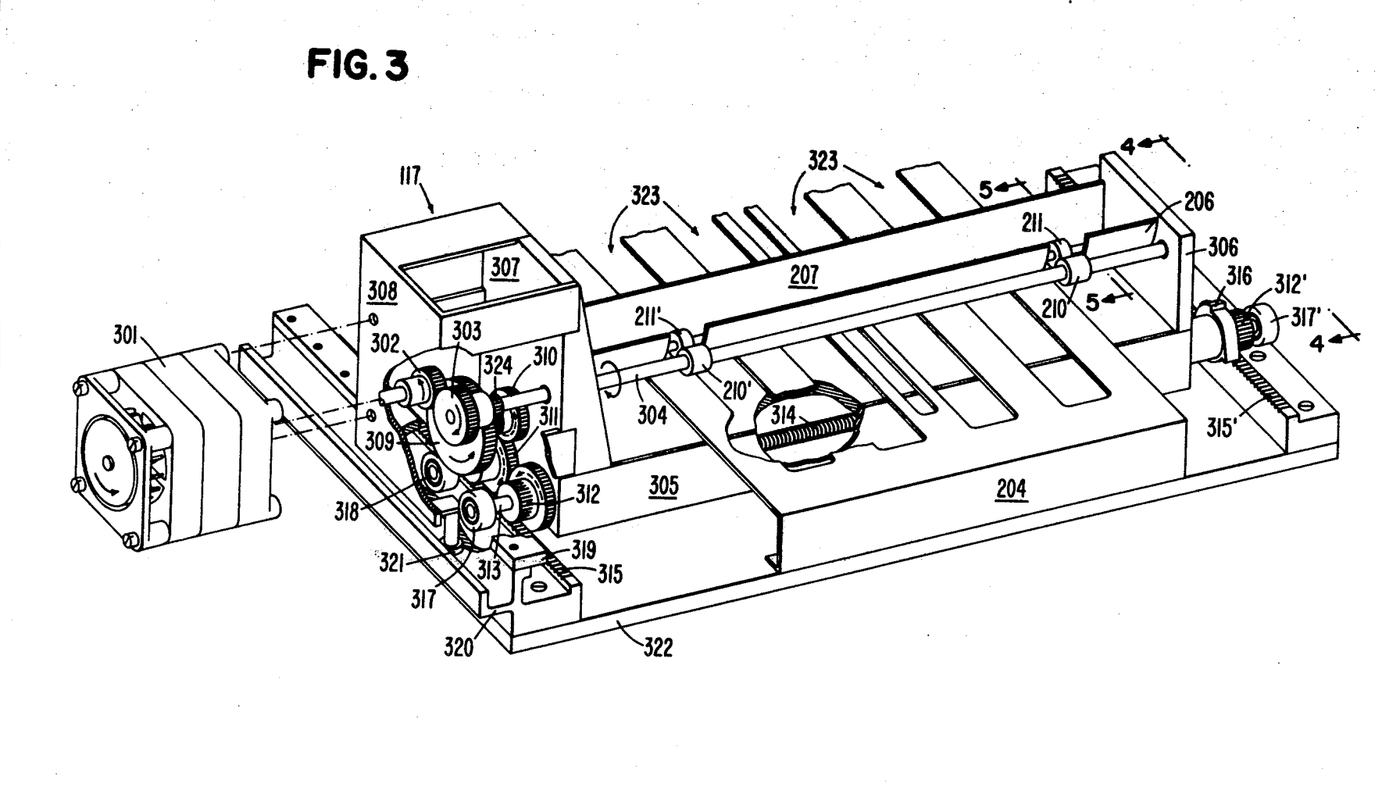
FIG. 3 is a detailed isometric view of the deflector unit of the collator and its guiding system.

FIG. 3 shows in some more detail the deflector unit 117 with its drive and guiding system. The deflector unit 117 which has already been shown in FIGS. 1C and 2 consists of a deflector frame 305 with two flanges 306 and 307 extending perpendicularly at the frame's 305 ends. Flange 307 bears a gear box 308 to which a drive motor 301 is fixed.

The gearbox 308 contains a gear system driving the paper feed system of the deflector unit 117 as well as moving the deflector unit itself. The paper feed drive consists of the motor gear 302 which is fixed to the motor's 301 drive shaft, and the drive roll gear 303 fixed to the drive roll shaft 304 which is rotatably mounted in flanges 306 and 307. Drive roll shaft 304 bears driven drive rolls 210 and 210'. The paper is fed between this pair of drive rolls and an associated pair of backup rolls 211 and 211'. The copy to be fed is directed by the lower deflector guide 206 and the upper deflector guide 207 which have already been shown in FIG. 2.

A small gear 324 on drive roll shaft 304 drives a larger gear 309 constantly. This constantly driven arrangement of gears is defined by solid arrows on the respective gears in the drawings. Gear 310 being coaxial with gear 309 is driven by the latter over a switchable clutch which is shown in detail in FIG. 6. Gear 310 drives deflector drive pinion gear 312 over an intermediate gear 311. The direction of drive of these latter three gears is shown by broken arrows.

When the clutch between large gear 309 and gear 310 is engaged, deflector drive pinion gears 312 and 312', the latter being fixed to the opposite end of deflector drive shaft 313, meshing with gear racks 315 and 315', respectively, drive deflector unit 117 to the left end of the collator frame 322 under the first bin. Whereas the driving force is accomplished by gears 312 and 312' meshing with gear racks 315 and 315', the deflector unit 117 is guided by guide rolls 317, 317', and 318. Together with guide rail 319, rolls 317 and 318 and a similar arrangement on the other side of the deflecting unit maintains the vertical relation of the deflector unit with the bins. Lateral or horizontal guidance is accomplished by a horizontal guide roll 321 engaging a horizontal U-shaped guide rail 320.

Deflector drive spring 314 is fixed with one end to deflector frame 305 and with its other end to deflector drive shaft 313. Thus, when the deflector drive unit 117 is moved to its initial leftmost (FIG. 3) position, the deflector drive spring is wound up. As soon as the deflector drive unit 117 reaches this position, the clutch connecting large gear 309 with gear 310 is disengaged. Therefore, the rotation of gears 310, 311 and 312 is stopped as well as the movement of the deflector unit 117.

From now on, deflector unit 117 is moved by force of the biased deflector drive spring 314. Stepping from bin to bin (c.f. FIG. 2) is controlled by a ratchet disk 316 fixed to deflector drive shaft 313. The details of the ratchet mechanism are shown in FIG. 4 and described below.

Attached to the collator frame 322 is the main paper guide 204 for the copies as already shown in FIG. 2. This main guide 204 has longitudinal slits 323 into which fingers of lower deflector guide 206 extend.

It should be added that the produced copies are fed into the collator shown in FIG. 3 from the left upper corner and that the initial position of deflector unit 117 i.e., the position under the first bin, is in the leftmost upper end of the collator frame 322.

Figure 4:
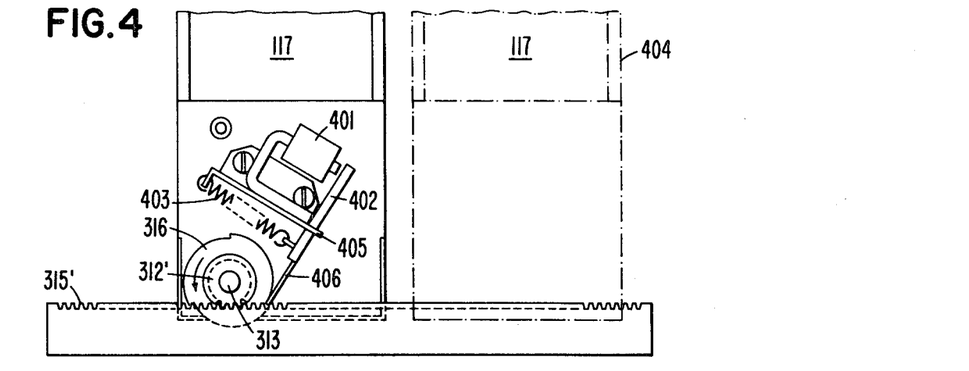
FIG. 4 shows a side view of the deflector unit in different positions as seen from direction 4—4 in FIG. 3.

FIG. 4 depicts a side view of the deflector unit 117 in two different positions from direction 4—4 in FIG. 3. It shows in detail the ratchet mechanism which controls the stepwise moving of the deflector unit from bin to bin. Deflector unit 117 is shown in its initial position by the broken dotted line 404 on the right side of the drawing. The solid line picture of deflector unit 117 defines any intermediate position under one of the bins. As already described in connection with FIG. 3, deflector drive pinion gear 312' meshes with gear rack 315'. The pinion gear 312' is fixed to the deflector drive shaft 313 as is the ratchet disk 316.

Ratchet disk 316 is blocked or released by a pawl which is actuated by a solenoid ratchet device. This consists essentially of a solenoid 401 activating an armature 402, which is pivotable around a dolly of frame 405 of the ratchet device and held by a tension spring 403 against ratchet disk 316. Upon activation of solenoid 401, armature 402 is attracted, disengaging pawl 406 from ratchet disk 316. Thus, ratchet disk 316 is able to rotate until it is brought to a stop by pawl 406 on armature 402 which, in the meantime, has been deactivated. Ratchet disk 316 is always forced against pawl 406 by tension of the deflector drive spring wound around deflector drive shaft 313. This arrangement was shown in detail in FIG. 3.

The number of ratchet teeth as well as the circumference of ratchet disk 316 and the radius of deflector drive pinion gear 312', both being fixed to deflector drive shaft 313, are chosen to let the deflector unit 117 step from one bin to the next one.

FIG. 5 shows a cross-section along the line 5—5 depicted in FIG. 3. It shows the deflector unit's 117 upper deflector guide 207 and the lower deflector guide 206 defining the copy path. Copies are driven through that path by drive roll 210 fixed to drive roll shaft 304 turning permanently in the direction shown by the arrow. The copy is held against drive roll 210 by backup roll 211 mounted to backup roll shaft 504. This shaft is mounted to an extension of the upper deflector guide 207 by a leaf spring 501, pressing the backup roll 211 against drive roll 210. Included in the deflector frame 305 is the deflector drive shaft 313 with the deflector drive spring 314 wound around it. Additionally, switch 502 is provided, the actuating arm 503 of which extends through one of the slits in the lower deflector guide 206 (see FIG. 3) into the copy path. This switch is used to provide one of the input signals for the logic circuits shown in FIGS. 9 and 10, discussed below.

Figure 6:
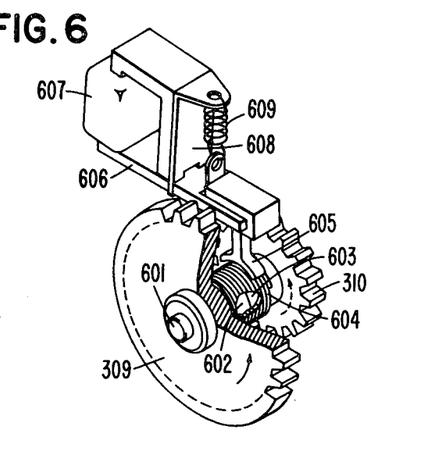
FIG. 6 depicts a detail of the deflector drive.

FIG. 6 shows a detail of the deflector drive which was already mentioned in the description of FIG. 3. Gear 309 is permanently driven by the deflector drive motor (301 in FIG. 3). Together with its hub 602, it is rotatably mounted on axle 601. Rotation occurs in counterclockwise direction, as depicted by the solid arrow. On the other end of the same axle 601, small gear 310 with its hub 603 is rotatably mounted. Around the hub 602 of the large gear 309, a clutch spring 604 is wound and fixed, at least with its end, thereto. The inner diameter of clutch spring 604 is slightly larger than the outer diameter of hub 603 of the small gear 310. Thus, the assembly made out of large gear 309, its hub 602 and clutch spring 604 can rotate without effecting small gear 310. T-shaped clutch actuator 605 is held in a short distance above the clutch spring 604 over the hub 603 of small gear 310. This is effected by tension spring 609 holding armature 606, which is pivotable around a dolly of frame 608, in its deactivated position. As soon as solenoid 607 is actuated, armature 606 is attracted and clutch actuator 605 pressed down onto the rotating clutch spring 604, coupling the hub 603 of the small gear 310 with the spring. Thus, large gear 309 and small gear 310 are coupled to each other, small gear 310 turning in the direction defined by the broken arrow. Upon deactivation of solenoid 607, clutch actuator 605 is released from clutch spring 604, whereupon small gear 310 is disengaged from large gear 309. As described in connection with FIG. 3, engagement of the clutch and driving of small gear 310 serves to move the deflector unit back into its initial position and simultaneously winds deflector drive spring 314 which afterwards serves as energy source for the deflector unit's stepping.

Figure 7A:
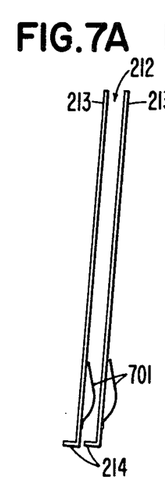
FIGS. 7A, 7B, and 7C show different copy retaining means in the bins.
Figure 7B:
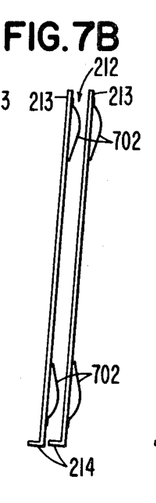
Figure 7C:
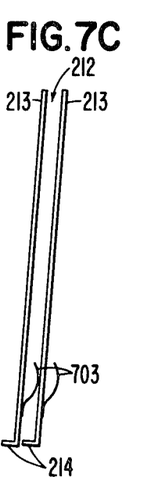

FIGS. 7A, 7B and 7C show different kinds of retaining means that are useful to hold the copies in each of the bins 212, consisting essentially of one or more relatively soft springs 701, 702, or 703 respectively fixed to the bin wall 213 opposite the lip 214. There can be more than one spring 701 along the width of the paper bin 212.

FIG. 7B shows an arrangement of two springs 702 above each other, whereas FIG. 7C depicts a single spring 703 again, but of different shape as spring 701 in FIG. 7A. Use of springs 701 and 702 allows reinsertion of a copy into the paper bin. This may be necessary to control the copy quality after producing the first copy.

FIG. 8 shows an arrangement which staggers copy sets of adjacent bins for easy separation. This is caused by a vertical displacement x of adjacent bins 212. Displacement x has to be chosen large enough to offset copy stacks sufficiently. On the other hand, it has to be small enough to allow proper copy feeding into both the lower and the upper bins 212. Copies are held in the bins 212 by retaining springs 703.

Figure 9:
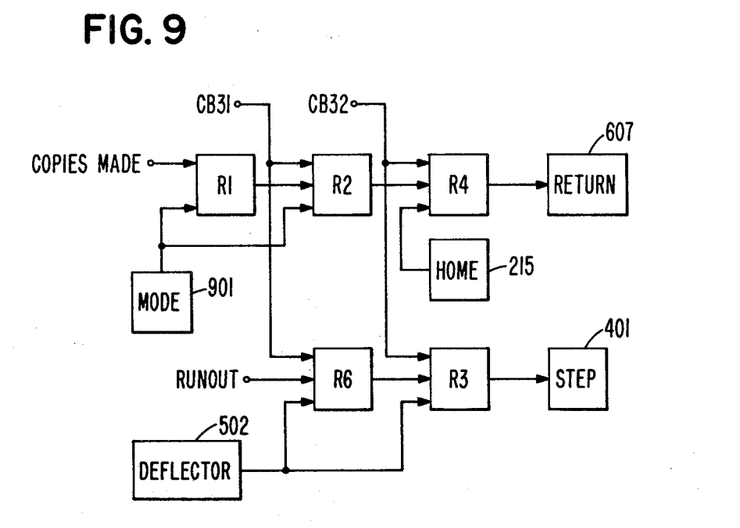
FIGS. 9 and 10 detail an example for the control circuits of the collator.

FIG. 9 shows a diagram of the relay logic used to control the bin-to-bin stepping movement of the deflector unit 117 and its return into its home position under the first bin when the collator is in its collate mode. The logic contains relays R1, R2, R3, R4, and R6 and receives discrete timing pulses CB31 and CB32 from the associated copier 101. CB31 occurs close to the beginning of a copy cycle, whereas CB32 is generated towards the end of a cycle. Additionally, copier 101 delivers the signal "runout" which provides an extended runout indication to allow continuing collator operation for a certain time after shutdown of the copier 101, and the signal "copies made" which indicates to the collator logic that the copier 101 has made the requested number of copies. This signal, in conjunction with the timing pulses CB31 and CB32 is used to activate the return solenoid 607 at the proper time when the collator is in the collate mode.

The signal "copies made" from the copier is stored in relay R1 and sequenced through relays R2 and R4 in accordance with timing pulses CB31 and CB32. Relays R1 and R2 are enabled by the mode switch 901 being in the "collate" position. Return solenoid 607, activating the clutch shown in FIG. 6, is turned on by relay R4 upon inputs of relay R2 and timing signal CB32. This results in return movement of the deflector unit 117 during which the spring 314 is wound, until the deflector unit 117 contacts the deflector-home switch 215. The output signal of this switch 215 deactivates relay R4 which, in turn, shuts off return solenoid 607.

Relay R6 inhibits relay R3 until a copy reaches the deflector unit 117. Then, the deflector switch 502 and timing signal CB32 activate relay R3 at the proper time to energize the step solenoid 401. This results in moving the deflector unit 117 to the next bin. As detailed in connection with FIG. 5, the deflector switch 502 provides an output signal upon feeding of a copy by deflector unit 117.

Figure 10:
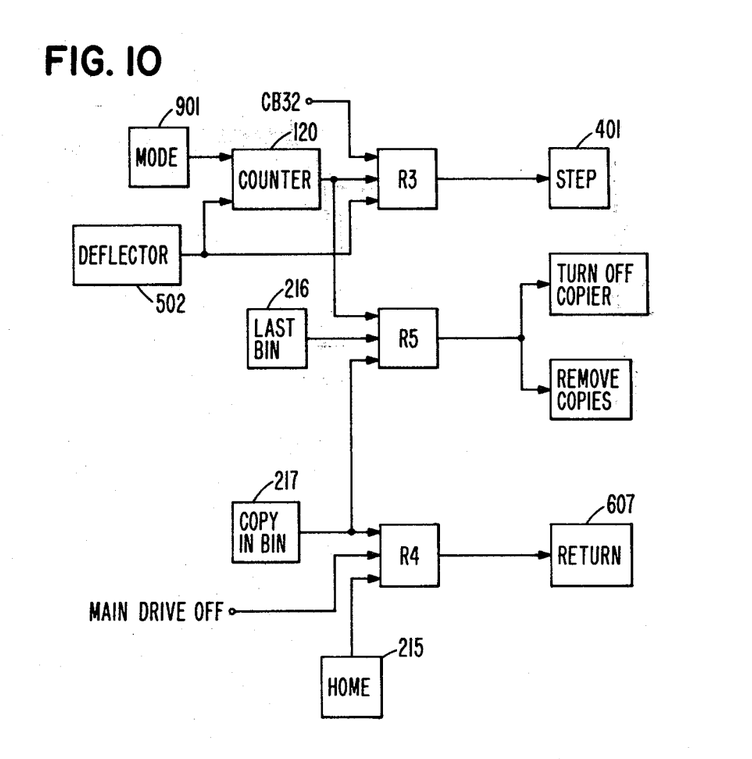

FIG. 10 shows the circuit used for the non-collating exit pocket mode of the collator. During this mode, each bin is filled up to a predetermined number of copies. The circuit contains the copies-in-bin counter 120 and receives the above-mentioned timing signal CB32 and the signal "main drive off" from the copier, the latter signal indicating when the main drive motor of the copier is off. As shown below, this information is used to inhibit the copy-in-bin switch 217 and to determine when the deflector unit 117 is to be returned to its home position at the end of a job.

The mode switch 901, set on "exit pocket" or "sort" mode, activates the counter 120. The counter 120, in turn, enables relay R3 when ten copies have passed the deflector switch 217. The number of copies to be chosen for the counter 120 depends on the size of the copy bins and the reliability required for the operation. For example, it may prove to be advantageous not to utilize the full bin capacity during the exit pocket mode, as the probability of a paper jam is much higher during insertion of the very last sheets up to the bin capacity. The deflector switch 502, together with timing signal CB32, activates relay R3 at the proper time to energize the step solenoid 401 shown in FIG. 4 which finally results in a step movement of the deflector unit 117 to the next bin. Relay R5 is activated when the deflector 117 reaches the position under the last, i.e. left-most bin in the arrangement shown in FIG. 2. This is sensed by the last-bin-position switch 216. Relay R5 causes the copier to stop and, at the same time, signals to the operator to remove the copies in the collator. This can be done by a simple light signal stating "remove copies" to the operator.

Relay R4 is activated when the copy-in-bin switch 217 indicates that the first bin is empty and, at the same time, the signal "main drive off" from the copier shows that the copier main drive motor is deactivated. Relay R4 then energizes the deflector return solenoid 607 which, as shown in detail in FIG. 6, results in continuous return movement of the deflector unit 117 until it contacts the deflector-home switch 215 when it reaches its initial position under the first bin. The output signal of the deflector-home switch 215 deactivates relay R4.

It is obvious for somebody skilled in the art to alter the circuit shown in FIGS. 9 and 10 to add any jam detection logic or to implement the collator control in a software program executed by a mini-computer.

The invention has been shown and described with reference to a detailed embodiment and several variations. However, it should be understood that other changes can be carried out by those skilled in the art without departing from spirit and scope of the invention.

What is claimed is:

1. A collator/sorter for distributing sheets comprising:
   a plurality of stationary, essentially vertically oriented sheet receiving bins,
   each of said bins having a bottom opening for enabling automatic sheet insertion and a top opening for enabling manual sheet removal,
   a sheet drive means located upstream of said bins,
   stationary, passive sheet guide means extending essentially horizontally under said bottom openings of said bins and extending upstream to a position adjacent to said sheet drive means, said guide means supporting said sheets for movement therealong under drive imparted to the sheets by said drive means,
   single sheet deflector means mounted for travelling along said sheet guide means including feeding means for positively feeding sheets from said sheet guide means directly upwardly into each of said bins, and means controlling said deflector means for selectively feeding predetermined numbers of sheets into said bins.

2. The collator/sorter of claim 1, said sheet receiving bins being dimensioned and spaced so that sheets can be manually removed simultaneously by one hand from said top bin openings.

3. The collator/sorter of claim 1, said sheet receiving bins having at least one wall parallel to the received sheets with at least a portion thereof shorter in length than the shortest inserted sheet.

4. The collator/sorter of claim 3, said sheet receiving bins having said bottom sheet insertion opening and said top removal opening in spaced, generally parallel relation, the spacing between said openings for each of said bins being shorter than the length of the shortest inserted sheet.

5. The collator/sorter of claim 1, said controlling means including means selectably operable either in a collate mode for feeding successive sheets into successive ones of said bins or in a sort mode for serially feeding predetermined numbers of said sheets into said bins and manual selecting means connected for causing said controlling means to operate in one of said modes.

6. The collator/sorter of claim 5, said controlling means including a counter activated in said sort mode for counting the number of sheets inserted into each of said bins, and means responsive to a predetermined count in said counter for advancing said sheet deflector for feeding into a next one of said bins.

7. The collator/sorter of claim 1, each of said sheet receiving bins being defined by spaced adjacent, at least approximately parallel walls, at least one of the walls having at its bottom end a lip extending generally perpendicular to the wall, but spaced from the adjacent wall to define said bottom opening of said bin.

8. The collator/sorter of claim 7, said sheet receiving bins being slightly inclined in direction of said wall having said lip.

9. The collator/sorter of claim 7, each of said sheet receiving bins including resilient, biased sheet holding means momentarily displaced by a sheet entering said bin, and thereafter causing said inserted sheet to register against said lip under the force of gravity.

10. The collator/sorter of claim 7, said lips of adjacent sheet receiving bins being offset for staggering sheets inserted into adjacent bins.

11. An improved unitary copy production apparatus with a frame comprising an imaging station for a document to be copied, a copy production portion, and a copy output portion, said copy output portion being a collator/sorter including:

a plurality of stationary, essentially vertically oriented copy receiving bins, each of said bins having a bottom opening for enabling copy insertion and a top opening for enabling manual copy removal, said top openings being in juxtaposition to said imaging station for facilitating manual removal of copies from said collator/sorter by an operator at said imaging station, and extending upstream to a position adjacent to said copy drive means, said guide means supporting said copies for movement therealong under drive imparted to the copies by said drive means, stationary, passive sheet guide means extending parallel to said bottom openings of said bins a copy drive means located upstream of said bins, single sheet deflector means mounted for travelling along said sheet guide means, including feeding means for receiving copies from said copy production portion and selectively directing received copies into said bins through said bottom openings.

12. The copy production apparatus of claim 11, said top openings of said copy receiving bins being located at an operating height, and dimensioned and spaced so that copies usually can be manually removed simultaneously by one hand.

13. The copy production apparatus of claim 11, the number of said copy receiving bins not exceeding ten and the copy capacity of each bin not exceeding twenty copies.

14. The copy production apparatus of claim 11, said copy receiving bins being at least partly in one dimension shorter than the length of the shortest inserted copy.

15. The copy production apparatus of claim 11, said control means including a counter activated in said sort mode for counting the number of copies inserted into each of said bins, and, when reaching a predetermined count, advancing said copy deflector for feeding into the next unfilled bin.

16. The copy production apparatus of claim 11, each of said copy receiving bins being defined by spaced adjacent, at least approximately parallel walls, at least one of the walls having at its bottom end a lip extending generally perpendicular to the wall, but spaced from the adjacent wall to define said bottom opening of said bin.

17. The copy production apparatus of claim 16, said copy receiving bins being slightly inclined in direction of said wall having said lip.

18. The copy production apparatus of claim 16, each of said copy receiving bins including resilient, biased copy holding means deflected by a copy entering said bin, and thereafter returning into its initial position for causing said inserted copy to register against said lip under the force of gravity.

19. The copy production apparatus of claim 16, said lips of adjacent copy receiving bins being offset for staggering copies inserted into adjacent bins.

20. The copy production apparatus of claim 11, said copy transport means including stationary copy transfer means extending essentially horizontally under said bottom openings of said bins.

21. The copy production apparatus of claim 20, said deflector means being a single copy deflector means mounted for travelling along said copy transfer means and operable for deflecting copies from said transfer means selectively into each of said bins.

22. The copy production apparatus of claim 11, further comprising:

selectable control means for controlling said deflector means either to operate in a collate mode feeding successive copies into adjacent bins, or to operate in a sort mode feeding said bins, one at a time, with a predetermined number of copies, and selecting means connected with said control means for manually selecting either of said modes.

* * * * *

UNITED STATES PATENT AND TRADEMARK OFFICE
CERTIFICATE OF CORRECTION

PATENT NO. : 4,141,546
DATED : February 27, 1979
INVENTOR(S) : Carl A. Queener

It is certified that error appears in the above-identified patent and that said Letters Patent are hereby corrected as shown below:

In Claim 11, line 14, after "tion" delete "and extending upstream to a position adjacent to said copy drive means, said guide means supporting said copies for movement therealong under drive imparted to the copies by said drive means," and insert --a copy drive means located upstream of said bins,--;

Claim 11, line 19, delete "a copy drive"

Claim 11, line 20, delete "means located upstream of said bins,"

Claim 11, line 19, after "bins", insert --and extending upstream to a position adjacent to said copy drive means, said guide means supporting said copies for movement therealong under drive imparted to the copies by said drive means,--.

Signed and Sealed this

Eleventh Day of September 1979

[SEAL]

Attest:

LUTRELLE F. PARKER
Attesting Officer    Acting Commissioner of Patents and Trademarks